United States Patent [19]

Jung et al.

[11] Patent Number: 5,527,938

[45] Date of Patent: Jun. 18, 1996

[54] (2-ARYLPROPYL)SILANES AND PREPARATION METHODS THEREOF

[75] Inventors: Il N. Jung; Bok R. Yoo, both of Seoul; Bong W. Lee, Kwangju; Seung H. Yeon, Kyungki-Do, all of Rep. of Korea

[73] Assignee: Korea Institute of Science and Technology, Seoul, Rep. of Korea

[21] Appl. No.: 277,219

[22] Filed: Jul. 19, 1994

[51] Int. Cl.$^6$ ..................................................... C07F 7/08
[52] U.S. Cl. ............................................ 556/487; 556/489
[58] Field of Search ..................................... 556/487, 489

[56] References Cited

U.S. PATENT DOCUMENTS

| | | | |
|---|---|---|---|
| 3,088,964 | 5/1963 | Ryan | 556/489 X |
| 4,873,011 | 10/1989 | Jung et al. | |
| 4,965,385 | 10/1990 | Jung et al. | |
| 5,075,477 | 12/1991 | Jung et al. | |
| 5,087,717 | 2/1992 | Jung et al. | |
| 5,233,069 | 8/1993 | Jung et al. | |
| 5,235,061 | 8/1993 | Jung et al. | |
| 5,235,083 | 8/1993 | Jung et al. | |
| 5,300,669 | 4/1994 | Akamatsu | 556/489 X |
| 5,302,734 | 4/1994 | Jung et al. | |
| 5,332,849 | 7/1994 | Jung et al. | |
| 5,338,876 | 8/1994 | Jung et al. | |

OTHER PUBLICATIONS

Hurd, "The Preparation of Vinyl and Allyl Chlorosilanes", *J. Am. Chem. Soc.*, Oct., 1945, vol. 67, pp. 1813–1814.
Chemical Abstract 15457i, V. F. Mironoy et al., "Synthesis and polymerization of compounds containing hydrogen at the silicon atom and an unsaturated radical", 1957.
Chemical Abstract 22325h, A. D. Petrov et al., "Catalytic disproportionation of alkyl(alkenyl)dichlorosilanes.", 1960.
Chemical Abstract 65564u, N. S. Nametkin et al., "Alkylation of aromatic compounds by allylsilane chlorides.", vol. 66, 1967.

*Primary Examiner*—Paul F. Shaver
*Attorney, Agent, or Firm*—Oblon, Spivak, McClelland, Maier & Neustadt

[57] ABSTRACT

The present invention relates to (2-arylpropyl)silanes represented by the formula (III) and a process for the preparation of the formula (III) by the Friedel-Crafts alkylation of various substituted aromatic compounds represented by the formula (I) with allylchlorosilanes as represented by the formula (II) in the presence of Lewis acid catalysts such as aluminum chloride.

$$R-Ar-R' \quad (I)$$

$$CH_2=CHCH_2-\underset{\underset{X^3}{|}}{\overset{\overset{X^1}{|}}{Si}}-X^2 \quad (II)$$

$$R-Ar-R' \quad X^1 \atop | \qquad | \atop CH_3-CH-CH_2-\underset{\underset{X^3}{|}}{Si}-X^2 \quad (III)$$

In the formulas (I) and (III), R and R' represent independently hydrogen, alkyl ($C_1$–$C_4$), phenoxy, fluoro, chloro, bromo, mercapto, mercaptomethyl and Ar represents phenyl ring, naphthalene ring, or biphenyl ring. $X^1$, $X^2$, and $X^3$ represent hydrogen or chloro group; and wherein formula (III) according to the present invention specifically excludes the compounds of the general formula (III) in which $X^1$, $X^2$ and $X^3$ are all chloro group, and R is hydrogen and R' is hydrogen, chloro or bromo, and $X^1$ is hydrogen and $X^2$ and $X^3$ are all chloro, and R and R' are all hydrogen.

25 Claims, No Drawings

(2-ARYLPROPYL)SILANES AND PREPARATION METHODS THEREOF

BACKGROUND OF THE INVENTION

1. Field of the Invention

The present invention relates to (2-arylpropyl)silanes represented by the formula (III) and a process for the preparation of the formula (III) by the Friedel-Crafts alkylation of substituted aromatic compounds represented by the formula (I) with allylchlorosilanes as represented by the formula (II) in the presence of Lewis acid catalysts such as aluminum chloride.

$$R-Ar-R' \quad (I)$$

$$CH_2=CHCH_2-\underset{\underset{X^3}{|}}{\overset{\overset{X^1}{|}}{Si}}-X^2 \quad (II)$$

$$\underset{\underset{X^3}{|}}{\overset{R-Ar-R'}{\underset{|}{CH_3-CH-CH_2-\overset{\overset{X^1}{|}}{Si}-X^2}}} \quad (III)$$

In the formulas (I) and (III), R and R' represent independently hydrogen, alkyl ($C_1$-$C_4$), phenoxy, fluoro, chloro, bromo, mercapto or mercaptomethyl, and Ar represents phenyl ring, naphthalene ring or biphenyl ring. $X^1$, $X^2$ and $X^3$ represent hydrogen or chloro group. In formula (III) according to the present invention specifically excludes the compounds of the general formula (III) in which $X^1$, $X^2$ and $X^3$ are all chloro group, and R is hydrogen and R' is hydrogen, chloro or bromo, and $X^1$ is hydrogen and $X^2$ and $X^3$ are all chloro, and R and R' are all hydrogen.

2. Description of the Prior Art

Hurd reported first the direct synthesis of allyldichlorosilane from allyl chloride and metallic silicon in 1945 (D. T. Hurd, J.Am. Chem. Soc., 67, 1813(1945)). When allyl chloride was reacted with a 9:1 Si—Cu alloy, a vigorous exothermic reaction occurred even at 250° C. The obtained condensate contained trichlorosilane, tetrachlorosilane, allyldichlorosilane, diallyldichlorosilane and allyltrichlorosilane due to the decomposition of allyl chloride during the reaction. This reaction has never been used on a large scale in industry, because of the decomposition of allyl chloride and the easy polymerization of diallyldichlorosilane at high temperature above 130° C.

Mironov and Zelinskii also reported that they obtained only 644 g of a mixture of allylchlorosilanes from the reaction of a 5:1 Si—Cu alloy with 2 kg of allyl chloride at 300° C. The product mixture contained 356 g of allyldichlorosilane, 185 g of allyltrichlorosilane, and 103 g of diallydichlorosilane (V. M. Mironov and D. N. Zelinskii, Isvest. Akad. Nauk S.S.S.R., Otdel Khim. Nauk 383(1957). The production of allyldichlorosilane and allyltrichlorosilane indicates that allyl chloride decomposed under the reaction conditions and dehydrochlorination or dechlorination were accompanied. This is why the yield was under 30%, indicating that the process was not economically feasible.

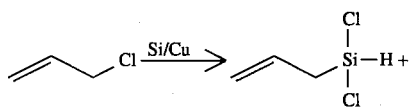

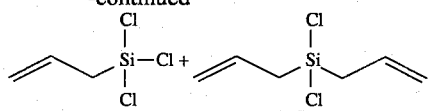

The present inventors reported a preparation method of allylchlorosilanes by directly reacting silicon metal simultaneously with allyl chloride and hydrogen chloride in the presence of copper catalyst at a temperature from 220° C. to 350° C. Allyldichlorosilane was obtained as the major product indicating one mole of each of the allyl chloride and hydrogen chloride reacted with the same silicon atom. When sufficient hydrogen chloride was added, diallyldichlorosilane was not formed. This eliminated the polymerization problem involved in the direct synthesis (Korean Patent Application 92-10292 (92.6.1.3)).

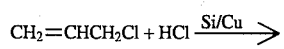

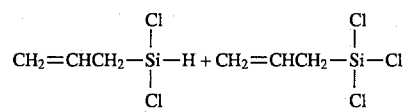

Petrov and his co-workers reported that allyldichlorosilane can be disproportionated to allylchlorosilane and allyltrichlorosilane in the presence of pyridine catalyst (A. D. Petrov and V. M. Vdovin, Izv. Akad. Nauk SSSR, Ser. Khim., 1960, 519).

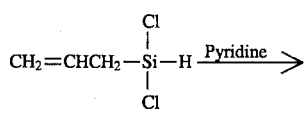

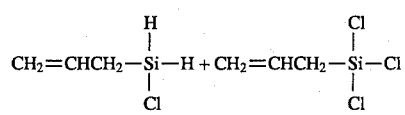

Nametkin and his co-workers reported that the Friedel-Crafts type addition of allylchlorosilanes to mono substituted benzenes to give 3-phenyl-1-silabutanes (N. S. Nametkin, V. M. Vdovin, E. S. Finkelshtein, V. D. Oppengeium and N. A. Chekalina, Izv. Akad. Nauk SSSR, Ser. Khim., 1966(11), 1998–2004). They reacted allyltrichlorosilane, allyldichlorosilane, allylmethyldichlorosilane or allyltrimethylsilane with benzene, chlorobenzene, bromobenzene or benzyltrichlorosilane in the presence of aluminum chloride to give (2-arylpropyl)silanes. The yield of 2-(phenyl)propyldichlorosilane from the reaction of allyldichlorosilane with benzene was 60%.

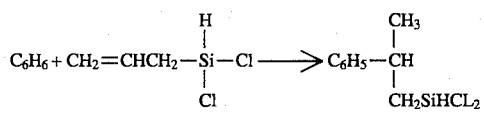

SUMMARY OF THE INVENTION

The present invention relates to (2-arylpropyl)silanes represented by the formula (III) and a process for the preparation of the same by the Friedel-Crafts alkylation of various substituted aromatic compounds represented by the formula (I) with allylchlorosilanes as represented by the formula (II) in the presence of Lewis acid catalysts such as aluminum chloride.

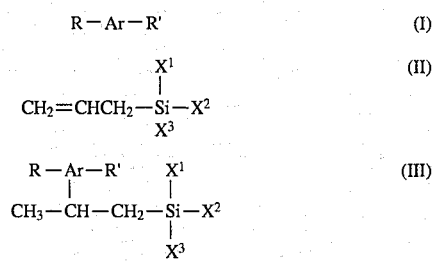

In the formulas (I) and (III), R and R' represent independently hydrogen, alkyl ($C_1$–$C_4$), phenoxy, fluoro, chloro, bromo, mercapto or mercaptomethyl and Ar represents phenyl ring, naphthalene ring or biphenyl ring. $X^1$, $X^2$ and $X^3$ represent hydrogen or chloro group. In formula (III) according to the present invention specifically excludes the compounds of the general formula (III) in which $X^1$, $X^2$ and $X^3$ are all chloro group, and R is hydrogen and R' is hydrogen, chloro or bromo, and $X^1$ is hydrogen and $X^2$ and $X^3$ are all chloro, and R and R' are all hydrogen.

The (2-arylpropyl)silanes producing alkylation reactions of the present invention can be run in standard laboratory glassware or commercial equipments, under inert atmosphere, with units for external heating and cooling, stirring, and for incremental addition of the starting materials, silanes or aromatic compounds. The reaction proceeds in neat condition, but it can be also carried out in organic solvents such as hydrocarbons or chlorinated hydrocarbons. The solid aromatic compounds such as naphthalene should be alkylated in solution. However, aromatic compounds or ethers are not suitable for this alkylation of the present invention. Useful Lewis acid catalysts include aluminum chloride, boron chloride, zinc chloride, titanium chloride, iron chloride, tin chloride, cadmium chloride and antimony chloride, but are not limited to them.

In a typical preparation, the compound (I) and the alkylation catalyst are placed in the reactor under inert atmosphere. The compound (II) is then slowly added to the solution with stirring. Excess compound (I) is recommended, otherwise double alkylated products will be produced. The reactions are exothermic and external cooling should be applied. After completion of addition, heating may be carried out for a certain period of time to complete the alkylation and then sodium chloride or tetrahydrofuran is added to deactivate the catalyst. Solids are filtered and the products are fractionally distilled at atmosphere or under vacuum.

The invention will be further illustrated by the following examples. It is, however, not intended that this invention will be limited by the examples.

EXAMPLE 1

To a 100 ml, three neck, round bottomed flask equipped with a mechanical stirrer, a dropping funnel and a reflux condenser, 0.9 g (0.007 mol) of aluminum chloride and 19.3 g (0.21 mole) of toluene were placed under the dry nitrogen atmosphere. With vigorous stirring, 10.0 g (0.07 mole) of allyldichlorosilane was added dropwise for 30 minutes and the reaction mixture was stirred for 1 hr at room temperature. Gas chromatographic analysis showed that no allyldichlorosilane was left. 2.0 g (0.03 mole) of sodium chloride was added and the solution was heated to 50° C. to quench the catalyst. Vacuum distillation of the solution gave 11.7 g (71%) of 2:1 mixture of 3-(4-methylphenyl)-1,1-dichloro-1-silabutane and 3-(2-methylphenyl)-1,1-dichloro-1-silabutane as a mixture of three isomers (boiling point: 73°–6° C./0.6 mmHg).

EXAMPLE 2 i) In the same apparatus and procedures as Example 1, 1.1 g (0.008 mol) of aluminum chloride and 27 g (0.26 mol) of o-xylene were reacted with 12.0 g (0.085 mol) of allyldichlorosilane at 0° C. for 1.5 hrs. Vacuum distillation of the solution gave 17.8 g (85%) of 5:1 mixture of 3-(3,4-dimethylphenyl)-1,1-dichloro-1-silabutane and 3-(2,3-dimethylphenyl)-1,1-dichloro-1-silabutane (boiling point: 95°–98° C./0.6 mmHg).

ii) In the same apparatus and procedures as Example 1, 0.65 g (0.005 mol) of aluminum chloride and 15.8 g (0.149 mol) of m-xylene were reacted with 7.0 g (0.049 mol) of allyldichlorosilane at 0° C. for 1.5 hrs. Vacuum distillation of the solution gave 8.8 g (73%) of 2.7:1 mixture of 3-(2,4-dimethylphenyl)-1,1-dichloro-1-silabutane and 3-(3,5-dimethylphenyl)-1,1-dichloro-1-silabutane (boiling point: 90°–93° C./0.6 mmHg).

iii) In the same apparatus and procedures as Example 1, 0.9 g (0.007 mol) of aluminum chloride and 37 g (0.349 mol) of p-xylene were reacted with 10 g (0.07 mol) of allyldichlorosilane at 0° C. for 1.5 hrs. Vacuum distillation of the solution gave 9.1 g (81%) of 3-(2,5-dimethylphenyl)-1,1-dichloro-1-silabutane (boiling point: 86°–9° C./0.6 mmHg).

EXAMPLE 3

In the same apparatus and procedures as Example 1, 1.13 g (0.009 mol) of aluminum chloride and 27 g (0.255 mol) of ethylbenzene were reacted with 12 g (0.085 mol) of allyldichlorosilane at 0° C. for 1 hr. Vacuum distillation of the solution gave 16.3 g (78%) of 1:2 mixture of 3-(2-ethylphenyl)-1,1-dichloro-1-silabutane and 3-(4-ethylphenyl)-1,1-dichloro-1-silabutane (boiling point: 80°–4° C./0.6 mmHg).

EXAMPLE 4

In the same apparatus and procedures as Example 1, 0.46 g (0.0035 mol) of aluminum chloride and 12.6 g (0.105 mol) of isopropylbenzene were reacted with 5 g (0.035 mol) of allyldichlorosilane at 0° C. for 1 hour. Vacuum distillation of the solution gave 6.5 g (71%) of 1:2 mixture of 3-(3-isopropylphenyl)-1,1-dichloro-1-silabutane and 3-(4-isopropylphenyl)-1,1-dichloro-1-silabutane (boiling point: 91°–4° C./0.6 mmHg).

EXAMPLE 5

In the same apparatus and procedures as Example 1, 0.46 g (0.0035 mol) of aluminum chloride and 11.8 g (0.105 mol) of chlorobenzene were reacted with 5 g (0.035 mol) of allyldichlorosilane at 25° C. for 1 hour. Vacuum distillation of the solution gave 5.7 g (63%) of 1:1 mixture of 3-(2-chlorophenyl)-1,1-dichloro-1-silabutane and 3-(4-chlorophenyl)-1,1-dichloro-1-silabutane (boiling point: 75°–8° C./0.6 mmHg).

EXAMPLE 6

In the same apparatus and procedures as Example 1, 0.46 g (0.0035 mol) of aluminum chloride and 21.98 g (0.14 mol) of bromobenzene were reacted with 5 g (0.035 mol) of allyldichlorosilane at 25° C. for 1 hour. Vacuum distillation of the solution gave 4.6 g (62%) of 1:1 mixture of 3-(3-bromophenyl)-1,1-dichloro-1-silabutane and 3-(4-bromophenyl)-1,1-dichloro-1-silabutane (boiling point: 93°–96° C./0.6 mmHg).

EXAMPLE 7

In the same apparatus and procedures as Example 1, 0.18 g (0.0014 mol) of aluminum chloride and 4.03 g (0.043 mol) of fluorobenzene were reacted with 2.0 g 0.0014 mol) of allyldichlorosilane at 25° C. for 1 hour. Vacuum distillation of the solution gave 2.0 g (60%) of 1:1 mixture of 3-(2-fluorophenyl)-1,1-dichloro-1-silabutane and 3-(4-fluorophenyl)-1,1-dichloro-1-silabutane (boiling point: 93°–96° C./0.6 mmHg).

EXAMPLE 8

In the same apparatus and procedures as Example 1, 0.46 g (0.0035 mol) of aluminum chloride and 16.2 g (0.105 mol) of biphenyl in 20 ml of n-hexane were reacted with 5 g (0.035 mol) of allyldichlorosilane at 50° C. for 1 hour. Vacuum distillation of the solution gave 8.5 g (83%) of 1:5 mixture of 3-(2-phenylphenyl)-1,1-dichloro-1-silabutane and 3-(4-phenylphenyl)-1,1-dichloro-1-silabutane (boiling point: 134°–8° C./0.6 mmHg).

EXAMPLE 9

In the same apparatus and procedures as Example 1, 0.46 g (0.0035 mol) of aluminum chloride and 17.8 g (0.105 mol) of diphenyl ether in 20 ml of n-hexane were reacted with 5 g (0.035 mol) of allyldichlorosilane at 35° C. for 1 hour. Vacuum distillation of the solution gave 8.02 g (74%) of 2:3 mixture of 3-(2-phenoxyphenyl)-1,1-dichloro-1-silabutane and 3-(4-phenoxyphenyl)-1,1-dichloro-1-silabutane (boiling point: 126°–130° C./0.6 mmHg).

EXAMPLE 10

In the same apparatus and procedures as Example 1, 0.46 g (0.0035 mol) of aluminum chloride and 13.6 g (0.105 mol) of naphthalene in 20 ml of carbon tetrachloride were reacted with 5 g (0.035 mol) of allyldichlorosilane at 25° C. for 1 hour. Vacuum distillation of the solution gave 8.5 g (83%) of 4:1 mixture of 3-(1-naphthyl)-1,1-dichloro-1-silabutane and 3-(2-naphthyl)-1,1-dichloro-1-silabutane (boiling point: 128°–132° C./0.6 mmHg).

The structures and NMR data of the alkylated products prepared as above are listed in Table I.

TABLE I

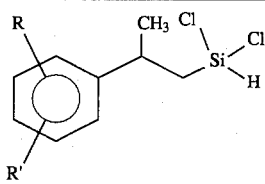

| Substituents | | NMR data (ppm) | | | | | |
|---|---|---|---|---|---|---|---|
| R | R' | CH₃ (d) | CH (hex.) | CH₂ (m) | Si—H (t) | aryl-H (m) | Others (R and R') |
| H | 2-CH₃ | 1.39 | 3.12 | 1.60–1.64 | 5.31 | 6.96–7.26 | 2.35 (s, 3H, CH₃) |
| H | 4-CH₃ | 1.40 | 3.14 | 1.60–1.64 | 5.34 | 6.96–7.26 | 2.37 (s, 3H, CH₃) |
| 2-CH₃ | 3-CH₃ | 1.23 | 3.12 | 1.57–1.65 | 5.34 | 6.96–7.10 | 2.24 and 2.26 (s, 3H, CH₃) |
| 3-CH₃ | 4-CH₃ | 1.39 | 3.12 | 1.59–1.64 | 5.34 | 6.96–7.10 | 2.26 and 2.28 (s, 3H, CH₃) |
| 2-CH₃ | 4-CH₃ | 1.36 | 3.42 | 1.58–1.66 | 5.39 | 7.00–7.17 | 2.32 and 2.36 (s, 3H, CH₃) |
| 3-CH₃ | 5-CH₃ | 1.39 | 3.11 | 1.59–1.64 | 5.35 | 6.86–7.00 | 2.33 (s, 6H, CH₃) |
| 2-CH₃ | 5-CH₃ | 1.36 | 3.41 | 1.55–1.72 | 5.40 | 6.90–7.06 | 2.34 (s, 6H, CH₃) |
| H | 2-CH₃CH₂ | 1.39 | 3.15 | 1.58–1.63 | 5.31 | 7.07–7.16 | 1.24 (t, 3H, CH₃), 2.64 (q, 2H, CH₂) |
| H | 4-CH₃CH₂ | 1.42 | 3.16 | 1.61–1.65 | 5.33 | 7.05–7.28 | 1.26 (t, 3H, CH₃), 2.66 (q, 2H, CH₂) |
| H | 3-(CH₃)₂CH | 1.40 | 3.15 | 1.59–1.63 | 5.32 | 7.08–7.28 | 1.26 (d, 6H, CH₃), 2.90 (hep. 1H, CH) |
| H | 4-(CH₃)₂CH | 1.42 | 3.17 | 1.61–1.65 | 5.31 | 7.06–7.29 | 1.28 (d, 6H, CH₃), 2.92 (hep. 1H, CH) |
| 2,3-Dibenzo— | | 1.57 | 4.09 | 1.85–1.93 | 5.49 | 7.39–8.17 | 7.39–8.17 (m, 4H, —CH=CH—CH=CH—) |
| 3,4-Dibenzo— | | 1.50 | 3.37 | 1.85–1.93 | 5.35 | 7.39–8.17 | 7.39–8.17 (m, 4H, —CH=CH—CH=CH—) |
| H | 2-F | 1.38 | 3.17 | 1.58–1.61 | 5.32 | 6.98–7.27 | |
| H | 4-F | 1.42 | 3.47 | 1.63–1.72 | 5.39 | 6.97–7.27 | |
| H | 2-Cl | 1.38 | 3.16 | 1.58–1.61 | 5.34 | 7.71–7.32 | |
| H | 4-Cl | 1.41 | 3.73 | 1.55–1.64 | 5.47 | 7.14–7.35 | |
| H | 2-Br | 1.38 | 3.15 | 1.57–1.60 | 5.35 | 7.11–7.46 | |
| H | 4-Br | 1.40 | 3.71 | 1.57–1.62 | 5.49 | 7.05–7.57 | |
| H | 2-Ph | 1.46 | 3.25 | 1.65–1.70 | 5.39 | 7.32–7.63 | 7.32–7.63 (m, 5H, phenyl-H) |
| H | 4-Ph | 1.47 | 3.28 | 1.65–1.76 | 5.39 | 7.23–7.51 | 7.23–7.51 (m, 5H, phenyl-H) |
| H | 2-PhO | 1.41 | 3.19 | 1.60–1.64 | 5.35 | 6.94–7.40 | 6.94–7.40 (m, 5H, phenoxy-H) |
| H | 4-PhO | 1.42 | 3.59 | 1.58–1.78 | 5.43 | 6.87–7.35 | 6.87–7.35 (m, 5H, phenoxy-H) |
| H | 2-SH | 1.43 | 3.51 | 1.59–1.73 | 5.31 | 7.15–7.50 | 3.31 (s, 1H, SH) |
| H | 4-SH | 1.44 | 3.56 | 1.59–1.72 | 5.48 | 7.15–7.50 | 3.35 (s, 1H, SH) |
| H | 2-CH₂SH | 1.38 | 3.13 | 1.60–1.65 | 5.31 | 7.10–7.50 | 1.69 (s, 1H, SH), 3.67 (s, 2H, CH₂) |
| H | 4-CH₂SH | 1.39 | 3.14 | 1.60–1.65 | 5.48 | 7.10–7.50 | 1.72 (s, 1H, SH), 3.71 (s, 2H, CH₂) |

EXAMPLE 11

In the same apparatus and procedures as Example 1, 0.20 g (0.0015 mol) of aluminum chloride and 9.66 g (0.105 mol) of toluene were reacted with 3 g (0.021 mol) of allyltrichlorosilane at 0° C. for 1 hr. Vacuum distillation of the solution gave 3.2 g (71%) of 1:3 mixture of 3-(2-methylphenyl)-1,1,1-trichloro-1-silabutane and 3-(4-methylphenyl)-1,1,1-trichloro-1-silabutane (boiling point: 74°–76° C./0.6 mmHg).

EXAMPLE 11

In the same apparatus and procedures as Example 1, 0.20 g (0.0015 mol) of aluminum chloride and 5.40 g (0.048 mol) of chlorobenzene were reacted with 3 g (0.021 mol) of allyltrichlorosilane at 0° C. for 20 minutes. Vacuum distillation of the solution gave 3.0 g (65.2%) of 1:3 mixture of 3-(2-chlorophenyl)-1,1,1-trichloro-1-silabutane and 3-(4-chlorophenyl)-1,1,1-trichloro-1-silabutane (boiling point: 78°–80° C./0.6 mmHg).

The structures and NMR data of the compounds prepared using the same procedure as described in Example 11 and 12 are listed in Table II.

chlorosilane at 0° C. for 20 minutes. Vacuum distillation of the solution gave 1.8 g (42%) of 1:3 mixture of 3-(2-chlorophenyl)-1-chloro-1-silabutane and 3-(4-chlorophenyl)-1-chloro-1-silabutane (boiling point: 60°–61° C./0.6 mmHg).

The structures and NMR data of the compounds prepared using the same procedure as described in Example 13 are listed in Table III.

TABLE II

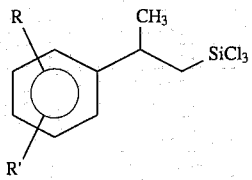

| Substituents | | NMR data (ppm) | | | | |
|---|---|---|---|---|---|---|
| R | R' | $CH_3$ (d) | CH (hex.) | $CH_2$ (m) | aryl-H (m) | Others (R and R') |
| H | 2-$CH_3$ | 1.49 | 3.27 | 1.82–1.95 | 7.11–7.32 | 2.42 (s, 3H, $CH_3$) |
| H | 4-$CH_3$ | 1.50 | 3.27 | 1.82–1.95 | 6.96–7.26 | 2.43 (s, 3H, $CH_3$) |
| 3-$CH_3$ | 4-$CH_3$ | 1.40 | 3.16 | 1.73–1.88 | 6.94–7.12 | 2.26 and 2.28 (s, 3H, $CH_3$) |
| 2-$CH_3$ | 4-$CH_3$ | 1.37 | 3.45 | 1.77–1.86 | 6.97–7.15 | 2.30 and 2.34 (s, 3H, $CH_3$) |
| 2-$CH_3$ | 4-$CH_3$ | 1.39 | 3.26 | 1.74–1.89 | 6.95–7.10 | 2.29 and 2.33 (s, 3H, $CH_3$) |
| 3-$CH_3$ | 5-$CH_3$ | 1.37 | 3.55 | 1.77–1.85 | 6.93–7.15 | 2.29 and 2.30 (s, 3H, $CH_3$) |
| 2-$CH_3$ | 5-$CH_3$ | 1.37 | 3.53 | 1.73–1.88 | 7.03–7.11 | 2.32 and 2.33 (s, 3H, $CH_3$) |
| H | 2-$CH_3CH_2$ | 1.44 | 3.20 | 1.74–1.89 | 7.10–7.15 | 1.24 (t, 3H, $CH_3$), 2.66 (q, 2H, $CH_2$) |
| H | 4-$CH_3CH_2$ | 1.45 | 3.21 | 1.76–1.91 | 7.04–7.23 | 1.27 (t, 3H, $CH_3$), 2.66 (q, 2H, $CH_2$) |
| H | 3-$(CH_3)_2CH$ | 1.42 | 3.21 | 1.70–1.87 | 7.03–7.24 | 1.23 (d, 6H, $CH_3$), 2.89 (hep, 1H, CH) |
| H | 4-$(CH_3)_2CH$ | 1.43 | 3.22 | 1.70–1.87 | 7.03–7.24 | 1.25 (d, 6H, $CH_3$), 2.90 (hep, 1H, CH) |
| 2,3-Dibenzo— | | 1.80 | 4.29 | 1.93–2.23 | 7.30–8.41 | 7.30–8.41 (m, 4H, —CH=CH—CH=CH—) |
| 3,4-Dibenzo— | | 1.81 | 3.47 | 1.93–2.23 | 7.30–8.41 | 7.30–8.41 (m, 4H, —CH=CH—CH=CH—) |
| H | 2-F | 1.42 | 3.18 | 1.80–1.94 | 6.97–7.28 | |
| H | 4-F | 1.44 | 3.59 | 1.85–1.95 | 6.97–7.28 | |
| H | 2-Cl | 1.42 | 3.19 | 1.77–1.89 | 7.12–7.32 | |
| H | 4-Cl | 1.43 | 3.67 | 1.80–1.84 | 7.12–7.32 | |
| H | 2-Br | 1.42 | 3.18 | 1.82–1.94 | 6.98–7.19 | |
| H | 4-Br | 1.43 | 3.57 | 1.82–1.95 | 6.98–7.19 | |
| H | 2-Ph | 1.46 | 3.36 | 1.84–1.90 | 7.28–7.60 | 7.28–7.60 (phenyl-H) |
| H | 4-Ph | 1.47 | 3.37 | 1.83–1.97 | 7.19–7.48 | 7.19–7.48 (phenyl-H) |
| H | 2-PhO | 1.41 | 3.30 | 1.83–1.88 | 6.90–7.37 | 6.90–7.37 (phenoxy-H) |
| H | 4-PhO | 1.42 | 3.68 | 1.77–1.97 | 6.85–7.29 | 6.85–7.29 (phenoxy-H) |
| H | 2-SH | 1.41 | 3.34 | 1.79–1.90 | 7.20–7.52 | 3.31 (s, 1H, SH) |
| H | 4-SH | 1.42 | 3.62 | 1.80–1.87 | 7.20–7.52 | 3.35 (s, 1H, SH) |
| H | 2-$CH_2SH$ | 1.47 | 3.28 | 1.80–1.88 | 7.08–7.45 | 1.67 (s, 1H, SH), 3.35 (s, 2H, $CH_2$) |
| H | 4-$CH_2SH$ | 1.48 | 3.29 | 1.80–1.88 | 7.08–7.45 | 1.74 (s, 1H, SH), 3.71 (s, 2H, $CH_2$) |

EXAMPLE 13

In the same apparatus and procedures as Example 1, 0.40 g (0.003 mol) of aluminum chloride and 10.00 g (0.109 mol) of toluene were reacted with 2.33 g (0.022 mol) of allyl-

TABLE III

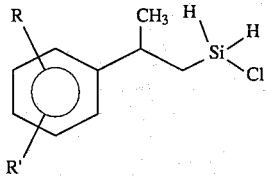

| Substituents | | NMR data (ppm) | | | | | |
|---|---|---|---|---|---|---|---|
| R | R' | $CH_3$ (d) | CH (hex.) | $CH_2$ (m) | $SiH_2$ (t) | aryl-H (m) | Others (R and R') |
| H | H | 1.36 | 3.07 | 1.40–1.45 | 4.59 | 6.94–7.26 | |
| H | 2-$CH_3$ | 1.26 | 3.06 | 1.40–1.44 | 4.57 | 6.90–7.25 | 2.35 (s, 3H, $CH_3$) |
| H | 4-$CH_3$ | 1.37 | 3.06 | 1.40–1.44 | 4.58 | 6.90–7.25 | 2.34 (s, 3H, $CH_3$) |

TABLE III-continued

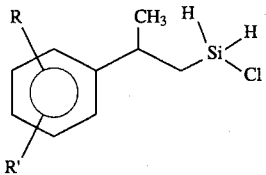

| Substituents | | NMR data (ppm) | | | | | |
|---|---|---|---|---|---|---|---|
| R | R' | CH$_3$ (d) | CH (hex.) | CH$_2$ (m) | SiH$_2$ (t) | aryl-H (m) | Others (R and R') |
| 2-CH$_3$ | 3-CH$_3$ | 1.18 | 3.04 | 1.38–1.43 | 4.59 | 6.96–7.16 | 2.25 and 2.27 (s, 3H, CH$_3$) |
| 3-CH$_3$ | 4-CH$_3$ | 1.29 | 3.04 | 1.38–1.43 | 4.69 | 6.96–7.16 | 2.26 and 2.27 (s, 3H, CH$_3$) |
| 2-CH$_3$ | 4-CH$_3$ | 1.27 | 3.16 | 1.39–1.42 | 4.60 | 7.00–7.15 | 2.33 and 2.38 (s, 3H, CH$_3$) |
| 3-CH$_3$ | 5-CH$_3$ | 1.28 | 3.05 | 1.39–1.42 | 4.59 | 6.95–7.12 | 2.36 (s, 6H, CH$_3$) |
| 2-CH$_3$ | 5-CH$_3$ | 1.27 | 3.29 | 1.35–1.50 | 4.50 | 6.98–7.09 | 2.32 and 2.33 (s, 3H, CH$_3$) |
| H | 2-Cl | 1.28 | 3.05 | 1.34–1.43 | 4.59 | 7.11–7.36 | |
| H | 4-Cl | 1.30 | 3.50 | 1.34–1.43 | 4.62 | 7.11–7.36 | |
| H | 2-Ph | 1.33 | 3.07 | 1.37–1.49 | 4.58 | 7.35–7.65 | 7.35–7.65 (s, 5H, phenyl-H) |
| H | 4-Ph | 1.34 | 3.08 | 1.37–1.49 | 4.59 | 7.25–7.55 | 7.35–7.65 (s, 5H, phenyl-H) |

What is claimed is:

1. A compound represented by the formula (III):

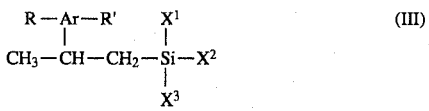

wherein R and R' represent independently hydrogen, alkyl (C$_1$–C$_4$), phenoxy, fluoro, chloro, bromo, mercapto or mercaptomethyl; Ar represents phenyl ring, naphthalene ring or biphenyl ring; and X$^1$, X$^2$ and X$^3$ represent independently hydrogen or chloro; and wherein formula (III) according to the present invention specifically excludes the compounds of the general formula (III) in which X$^1$, X$^2$ and X$^3$ are all chloro group, and R is hydrogen and R' is hydrogen, chloro or bromo, and X$^1$ is hydrogen and X$^2$ and X$^3$ are all chloro, and R and R' are all hydrogen.

2. The compound in accordance with claim 1, wherein R is hydrogen and R' is methyl.

3. The compound in accordance with claim 1, wherein R is hydrogen and R' is ethyl.

4. The compound in accordance with claim 1, wherein R is hydrogen and R' is isopropyl.

5. The compound in accordance with claim 1, wherein R is hydrogen and R' is halogen.

6. The compound in accordance with claim 1, wherein R is hydrogen and R' is phenyl.

7. The compound in accordance with claim 1, wherein R is hydrogen and R' is phenoxy.

8. The compound in accordance with claim 1, wherein R is hydrogen and R' is mercapto (—SH).

9. The compound in accordance with claim 1, wherein R is hydrogen and R' is mercaptomethyl (—CH$_2$SH).

10. The compound in accordance with claim 1, wherein R and R' are independently alkyl (C$_1$–C$_4$).

11. The compound in accordance with claim 1, wherein X$^1$ is hydrogen, and X$^2$ and X$^3$ are chloro.

12. The compound in accordance with claim 1, wherein X$^1$, X$^2$, and X$^3$ are all chloro.

13. The compound in accordance with claim 1, wherein X$^1$ and X$^2$ are hydrogen and X$^3$ is chloro.

14. The compound in accordance with claim 1, wherein R is hydrogen and R' is hydrogen, alkyl (C$_1$–C$_4$), phenoxy, fluoro, chloro, bromo, mercapto or mercaptomethyl at ortho-, meta- or para position of the phenyl ring and X$^1$ is hydrogen and X$^2$ and X$^3$ are chloro.

15. The compound in accordance with claim 1, wherein R is hydrogen and R' is hydrogen, alkyl (C$_1$–C$_4$), phenoxy, fluoro, chloro, bromo, mercapto or mercaptomethyl at ortho-, meta- or para position of the phenyl ring, and X$^1$, X$^2$ and X$^3$ are all chloro group.

16. The compound in accordance with claim 1, wherein R is hydrogen and R' is hydrogen, alkyl (C$_1$–C$_4$), phenoxy, fluoro, chloro, bromo, mercapto or mercaptomethyl at ortho-, meta-, or para position of the phenyl ring, and X$^1$ and X$^2$ are hydrogen and X$^3$ is chloro group.

17. The compound in accordance with claim 1, wherein R and R' are alkyl (C$_1$–C$_4$) and X$^1$ is hydrogen and X$^2$ and X$^3$ are chloro group.

18. The compound in accordance with claim 1, wherein R and R' are alkyl (C$_1$–C$_4$), and X$^1$, X$^2$ and X$^3$ are all chloro group.

19. The compound in accordance with claim 1, wherein R and R' are alkyl (C$_1$–C$_4$), and X$^1$ and X$^2$ are hydrogen, and X$^3$ is chloro group.

20. The compound in accordance with claim 1, wherein R—Ar—R' is naphthalene, and X$^1$ is hydrogen, and X$^2$ and X$^3$ are chloro group.

21. The compound in accordance with claim 1, wherein R—Ar—R' is naphthalene, and X$^1$, X$^2$ and X$^3$ are all chloro group.

22. The compound in accordance with claim 1, wherein R—Ar—R' is naphthalene, and X$^1$ and X$^2$ are hydrogen, and X$^3$ is chloro group.

23. A method for preparing (2-arylpropyl)silanes represented by the formula (III) comprising the Friedel-Crafts alkylation of a substituted aromatic compound represented by the formula (I) with a allylchlorosilane as represented by the formula (II) in the presence of Lewis acid catalyst:

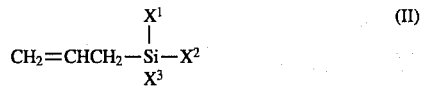

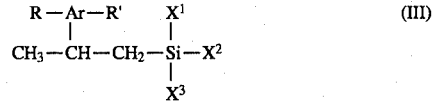

wherein R and R' represent independently hydrogen, alkyl (C$_1$–C$_4$), phenoxy, fluoro, chloro, bromo, mercapto or mercaptomethyl; Ar represents phenyl ring, naphthalene ring or biphenyl ring; and $X^1$, $X^2$ and $X^3$ represent independently hydrogen or chloro; and wherein formula (III) according to the present invention specifically excludes the compounds of the general formula (III) in which $X^1$, $X^2$ and $X^3$ are all chloro group, and R is hydrogen and R' is hydrogen, chloro or bromo, and $X^1$ is hydrogen and $X^2$ and $X^3$ are all chloro, and R and R' are all hydrogen.

24. The method in accordance with claim 23, wherein the reaction temperature is from 0° C. to 50° C.

25. The method in accordance with claim 23, wherein the catalyst is aluminum chloride.

* * * * *